United States Patent [19]
Beran et al.

[11] Patent Number: 5,287,851
[45] Date of Patent: Feb. 22, 1994

[54] ENDOTRACHEAL TUBE CONNECTOR WITH INTEGRAL PNEUMOTACH TRANSDUCER

[76] Inventors: Anthony V. Beran, 1472 La Loma Dr., Santa Ana, Calif. 92705; Gordon Y. Shigezawa, 34 Cresthaven, Irvine, Calif. 92714

[21] Appl. No.: 757,731
[22] Filed: Sep. 11, 1991
[51] Int. Cl.[5] .................. A61M 16/00; A62B 7/00; F16K 31/02; A61B 5/08
[52] U.S. Cl. .................. 128/204.23; 128/204.25; 128/725; 73/716; 73/861.52; 73/861.63
[58] Field of Search ............ 128/204.18, 204.22, 128/204.23, 205.23, 207.14, 207.16, 911, 912, DIG. 26, 719, 724, 722, 725, 204.25; 73/23.27, 23.29, 23.4, 29.03, 30.02, 31.04, 31.06, 861.42, 861.44, 861.45, 861.52, 861.61, 715, 720, 716, 861.63

[56] References Cited
U.S. PATENT DOCUMENTS

| | | |
|---|---|---|
| 3,927,670 | 12/1975 | Turney et al. ............ 128/719 |
| 3,960,142 | 6/1976 | Elliott et al. .............. 73/205 |
| 4,178,919 | 12/1979 | Hall ........................ 128/719 |
| 4,322,980 | 4/1982 | Suzuki et al. ............ 73/727 |
| 4,581,942 | 4/1986 | Ogura et al. ............ 128/719 |
| 4,723,543 | 2/1988 | Beran ...................... 128/207.14 |
| 4,815,459 | 3/1989 | Beran ...................... 128/207.14 |
| 4,884,460 | 12/1989 | Nowacki et al. .......... 73/861.52 |
| 4,932,269 | 6/1990 | Cammarata, III et al. .. 73/861.61 |
| 4,966,141 | 10/1990 | Bacaner et al. .......... 128/207.14 |
| 5,052,400 | 10/1991 | Dietz ....................... 128/722 |
| 5,134,886 | 8/1992 | Ball ........................ 73/718 |

Primary Examiner—J. Reed Fisher
Assistant Examiner—Kimberly L. Asher
Attorney, Agent, or Firm—Price, Gess & Ubell

[57] ABSTRACT

A pneumotach gas flow transducer having strain gauge pressure transducers disposed therein for disposition in a selected element or component of a ventilatory circuit. A differential pressure is communicated from the upstream and downstream sides of a flow restrictor in the element's passageway to the transducers via a barrier medium which fills holes in the element and contacts the transducer elements.

16 Claims, 6 Drawing Sheets

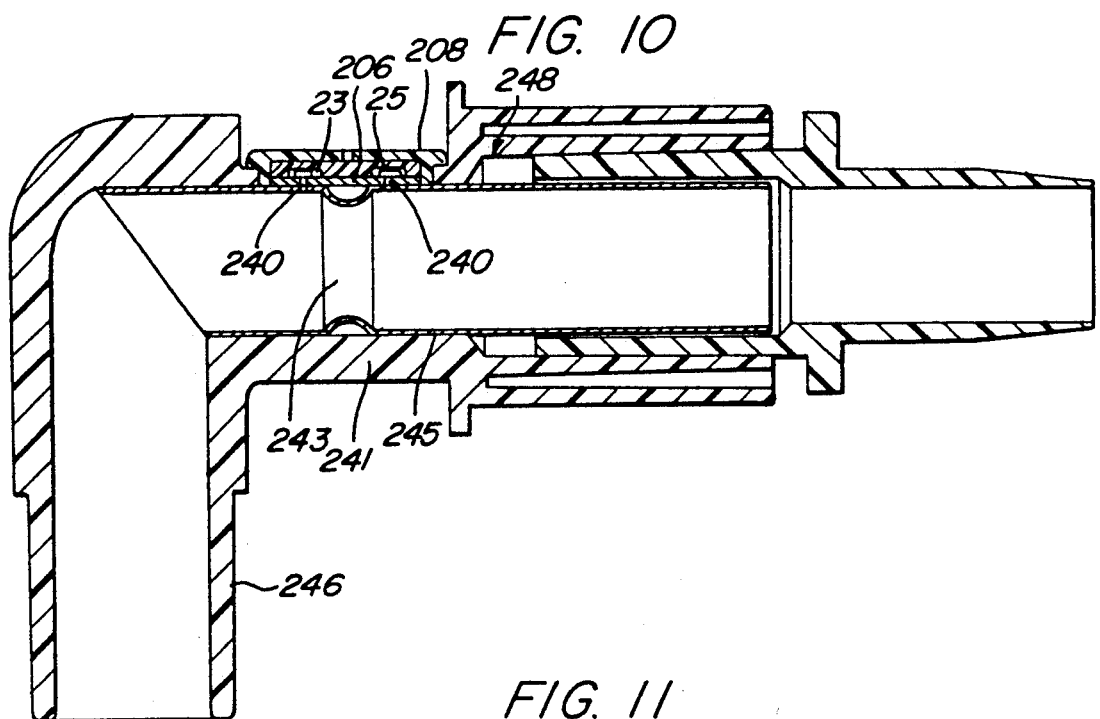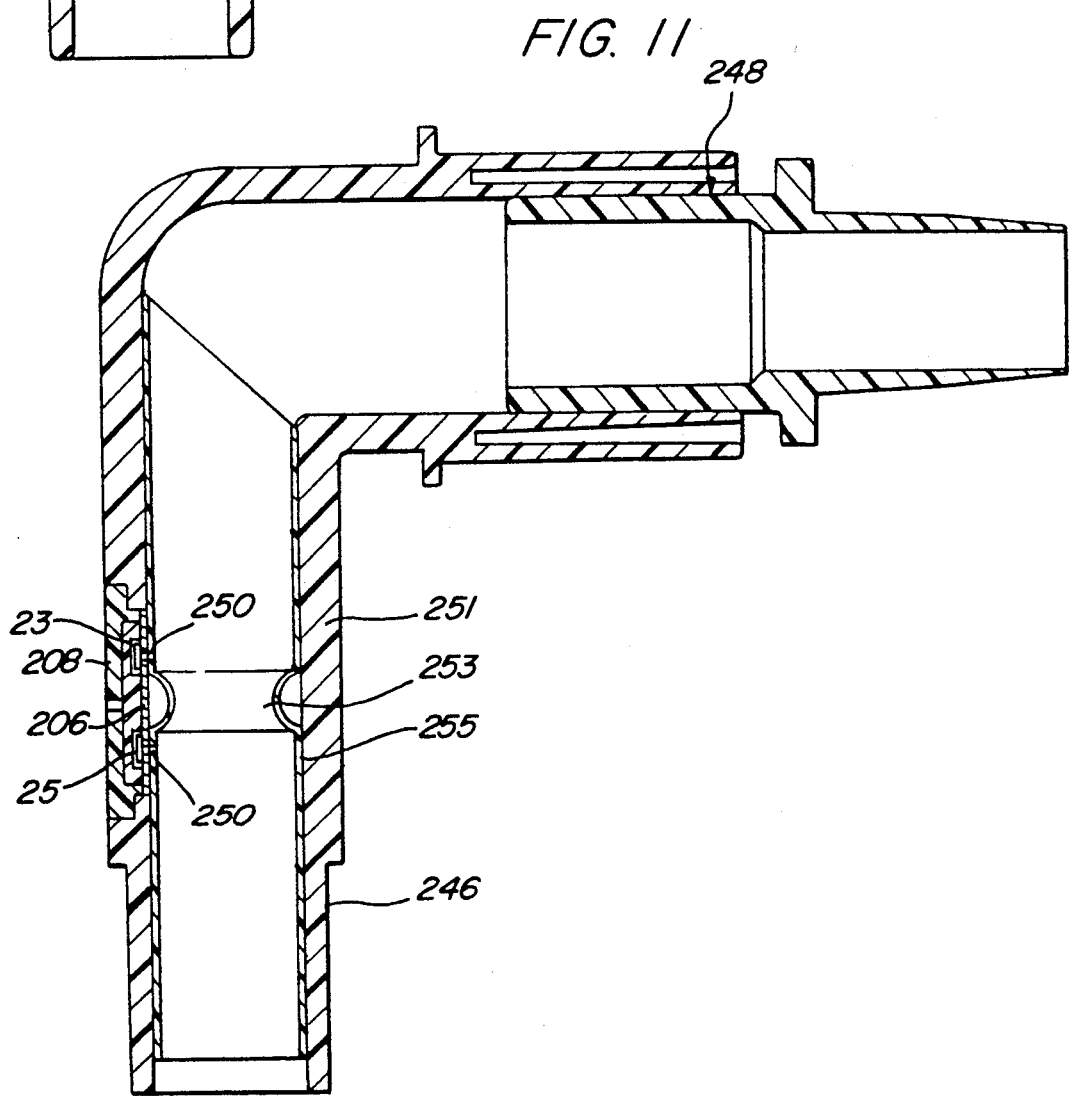

ENDOTRACHEAL TUBE CONNECTOR WITH INTEGRAL PNEUMOTACH TRANSDUCER

BACKGROUND OF THE INVENTION

1. Field of the Invention

The subject invention relates generally to medical devices and, more particularly, to an improved endotracheal tube connector incorporating a pneumotach transducer.

2. Description of Related Art

U.S. Pat. No. 4,815,459 discloses an endotracheal tube connector for use, for example, in interconnecting a respirator Y piece to an endotracheal tube. One embodiment of the endotracheal tube connector of the U.S. Pat. No. 4,815,459 patent employs a flow restrictor located in a conduit or lumen through the connector. Two passageways, one on either side of the flow restrictor, connect to respective tubes which may then be connected to a differential pressure transducer external to the connector.

The function of a pneumotach is based on measuring the pressure differential across a flow restrictor. The flow restrictor may be anything that reduces the cross-sectional area for flow of fluid through a conduit on axis with the flow. Provided that the flow through the restrictor and, for some length on both sides of the restrictor, is laminar, the pressure drop across the restrictor is linearly proportional to flow. Most pneumotachs suffer from some sort of nonlinearity at low and high flows due to turbulent flow, transducer resolution, and linearity limits, although that nonlinearity may be compensated for in the measuring instrument.

Ventilatory flow measurements are useful for calculating airway resistance (flow versus pressure). The flow measurement is often integrated, yielding inspiratory and expiratory volumes. Volume measurements are useful to calculate ventilatory compliance (volume versus pressure), a critical measurement of lung expandability. Real time volume measurements, coupled with real time gas composition measurements, yield whole body oxygen uptake, carbon dioxide excretion, and anesthetic uptake/excretion information. Cardiac output may be derived from uptake/excretion data and with central blood gas content measurements. Cardiac output and blood pressure measurements yield stroke volume, pulmonary vascular resistance, and systemic vascular resistance. Clearly, a convenient and accurate ventilatory flow measurement can form the basis for obtaining a large number of critical physiologic measurements. The flow measurement technique is relatively noninvasive, as are most of the other measurements.

As discussed above, U.S. Pat. No. 4,815,459 discloses that it is advantageous to incorporate a pneumotach flow restrictor in the lumen of an endotracheal tube connector. According to the embodiment disclosed in the U.S. Pat. No. 4,815,459 patent, such a flow restrictor may be in the form of a reduction of the inner diameter of the lumen over a predetermined length of the lumen. Several advantages of this construction have become evident:

1. The need to connect a separate pneumotach elsewhere in the ventilator circuit is eliminated, reducing ventilatory dead space and the risk of disconnection by eliminating additional in-line adapters and fittings.

2. The size of the flow restrictor may be tailored to give linear output over the expected range of flow for a given size connector. There is a correlation between the size of the patient, size of the endotracheal tube, corresponding size of the endotracheal tube connector, and ventilatory flows.

3. Conventional pneumotachs are clumsy devices usually requiring special connections, and add considerable weight to the ventilatory circuit. Some devices utilize an electrically heated screen restrictor to prevent water from condensing on the screen restrictor, thereby affecting the sensitivity of the flow measurement. The design of the endotracheal tube connector flow restrictor adds no additional device to the ventilator circuit (an endotracheal tube connector is needed regardless of the need for a flow measurement). The design of the in-line flow restrictor with generous remaining internal diameter has been shown to maintain calibration in the presence of water without heating.

While providing considerable improvement, the incorporation of a flow restrictor into an endotracheal tube connector according to the U.S. Pat. No. 4,815,459 patent still leaves certain drawbacks. In particular, the U.S. Pat. No. 4,815,459 embodiment, like other prior art pneumotach transducers, employs interconnection to an external differential pressure transducer through flexible pressure tubing.

In clinical application of these transducers, gas flows containing water or water vapor lead to condensation and/or collection of liquid water in the pressure tubes. The water or water vapor may be intentionally introduced into the gas stream from heated humidification or nebulization therapy. Alternately, the water may originate passively from humidity in the patient's expired air. Accumulation of liquid water in the tubes dampens the pressure measurement through the tube. Unequal water accumulation in both tubes creates unequal dampening of the pressure wave transmitted through the tube to the differential pressure transducer. The pressure sensed by the differential pressure transducer is, in turn, affected not only in magnitude, but also in the phase relationship between the pressure wave transmitted down each tube, in turn creating an error in the flow measurement. The magnitude of the flow measurement error depends on the amount, location, and viscosity of the water present in each tube, length and diameter of the pressure tubes, ventilatory rate, and displacement volumes of the pressure tubes and the pressure transducer.

Routine use of prior art pneumotachs in the clinical setting is difficult. Methods have been employed to periodically backflush the accumulated water back to the breathing circuit by application of positive pressure to both tubes exceeding the breathing circuit's pressure. The backflushing method requires user's interaction to assure that all water is purged within a limited purge time period and that minimal water is allowed to reform between purges.

The pressure tubing may also become disconnected either at the pneumotach or at the measuring instrument, causing leaks in the ventilator circuit. The tubes and pneumotach add to the bulk of material at the connection to the endotracheal tube that may cause disconnection of the endotracheal tube connector from the ventilator circuit or accidental extubation of the patient. The heated screen pneumotach adds the bulk of the heater lead wires and the additional temperature controller to the instrumentation system. The heated screen system may also inadvertently burn the patient or overheat the patient's inspired air.

SUMMARY OF THE INVENTION

It is therefore an object of the invention to eliminate interconnecting tube apparatus and its attendant problems;

It is another object of the invention to improve pneumotach apparatus;

It is another object of the invention to provide a pneumotach transducer apparatus which eliminates the problem of condensation and accumulation of water vapor in interconnecting tubes associated with prior pneumotach apparatus;

It is another object to provide such an apparatus which avoids dead space, is readily manufacturable, and retains all the advantages of the prior U.S. Pat. No. 4,815,459 device; and It is another object of the invention to improve endotracheal tube connectors.

According to the invention, the problems associated with prior art pneumotach interconnection tubing is eliminated by locating the pressure transducer as part of the breathing or ventilator circuit elements As one of many embodiments disclosed hereafter, the pressure transducer may be located in the endotracheal tube connector. Communication of pressure differential about a flow restrictor located in the endotracheal tube lumen is transmitted by a medium located in one or more holes in the connector. According to a further feature of the invention, the holes and medium communicate with pressure transducer elements In the preferred embodiment, two semiconductor elements are employed with concave sides facing respective holes.

Devices may be configured according to the invention as disposable units providing cross-contamination control and ease of use. The basic design of the device lends itself well to precision injection molding processes that can yield a device low enough in cost to justify disposal after one use. Such a disposable unit can be provided as a sterile unit, used on one patient, and cost effectively thrown away after use.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIGS. 10 and 11 are side sectional views of respective elbow pneumotach embodiments;

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide an economically manufacturable apparatus with optimal performance characteristics.

In a typical ventilator circuit, the separate inspiratory and expiratory ports of the mechanical ventilator are connected to a "Y" or "T" piece through two flexible tubes. Within the "Y" or "T" piece, the inspiratory and expiratory paths are commoned. All subsequent connections between the "Y" and the endotracheal tube conform to dimensions of a standardized tapered connection for ventilation circuits. An in-line connector or a right angle elbow may be connected between the common "Y" or "T" piece port and the endotracheal tube connector. The in-line or elbow connectors employ a male tapered fitting that inserts into the common "Y" female taper and a female taper that fits the male tapered fitting of the endotracheal tube connector. The endotracheal tube connector adapts the standardized ventilator circuit connection to the internal diameter of its matched endotracheal tube.

The pneumotach is best placed in the ventilator circuit where air flow is bidirectional (inspiratory and expiratory directions). This placement allows measurement of inspiratory and expiratory flows with one pneumotach rather than using separate devices in each path. Possible pneumotach placements include:

1. In the common port of the "Y" or "T" piece.
2. In an in-line adapter connected to the common port of the "Y" or "T" piece.
3. In the elbow.
4. In the endotracheal tube connector.
5. Between the endotracheal tube connector and the endotracheal tube.

ENDOTRACHEAL TUBE CONNECTOR PNEUMOTACH

Figure 1:
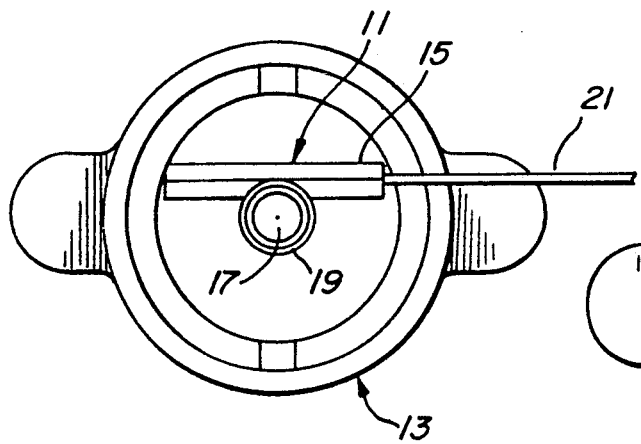
FIG. 1 is a front plan view of an endotracheal tube connector according to the preferred embodiment.
Figure 2:
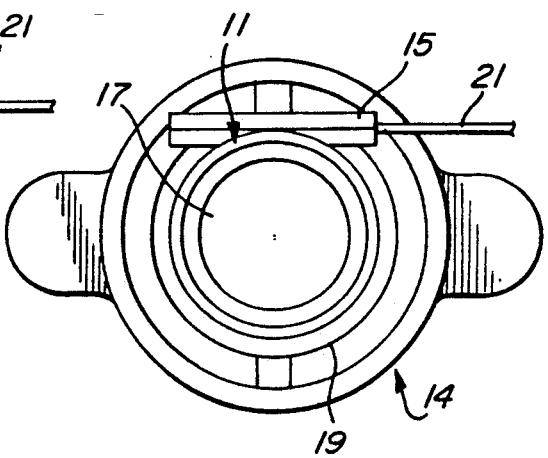
FIG. 2 is a front plan view of a second endotracheal tube connector according to the preferred embodiment.

FIG. 1 shows the transducer assembly 11 of the preferred embodiment as viewed from the patient end of an endotracheal tube connector 13. FIG. 2 illustrates the transducer assembly 11 on a larger size endotracheal tube connector 14. The transducer assembly 11 includes a rectangular housing 15 over the lumen 17 of the endotracheal tube (ET) connector 13. An interconnecting cable 21 exits the rectangular housing 15 to one side of the ET connector 13.

Figure 3:
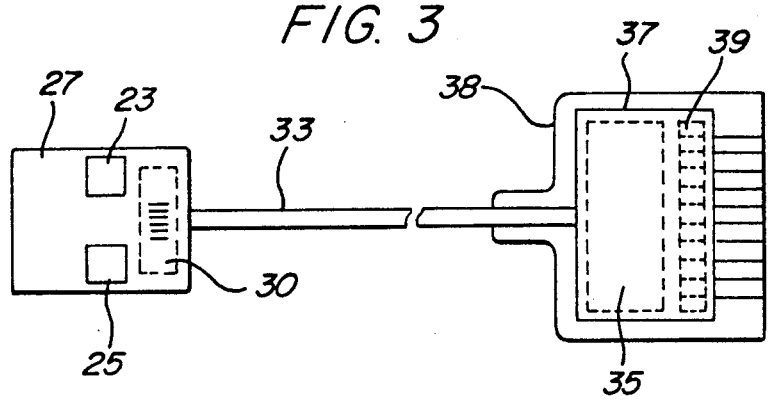
FIG. 3 is a top view of the pressure transducer apparatus according to the preferred embodiment.

FIG. 3 illustrates the differential transducer apparatus of the transducer assembly 11 of the preferred embodiment in more detail. First and second transducers 23, 25 are mounted on a substrate material 27, which is preferably alumina. The substrate 27 is located within the housing 15. The transducers 23, 25 are preferably semiconductor strain gauge devices wherein the strain gauge elements are incorporated into chips of silicon.

The side of each transducer 23, 25 facing the substrate 27 is etched to form a diaphragm, as known in the art.

Electrical connection to each transducer 23, 25 is made by wire bonding (thermocompression or ultrasonic) to pads deposited on the alumina substrate 27 by thick or thin film techniques. The substrate pads lead out to a lead termination area 30 to which is bonded the electrical conductors of the flat interconnection cable 21.

As is known in the art, semiconductor strain gauges, such as gauges 23, 25, must be trimmed for sensitivity, offset, and temperature compensation. Trimming is accomplished by attaching fixed resistances to the strain gauge elements 23, 25. According to the preferred embodiment, it is advantageous to place the trimming resistances 35 on the substrate 27, although they can also be located elsewhere, e.g. in plug 38. The resistances 35 are deposited on the alumina substrate 27 and laser trimmed to compensate each transducer 23, 25. An interconnect device 39 is provided at the end of cable 33 for attachment of a conventional extension cable connector leading to a measuring instrument.

Figure 4:
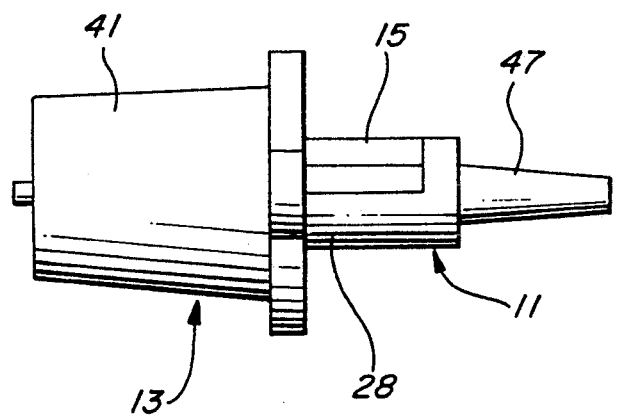
FIG. 4 is a side view of the endotracheal tube connector of FIG. 1.
Figure 5:
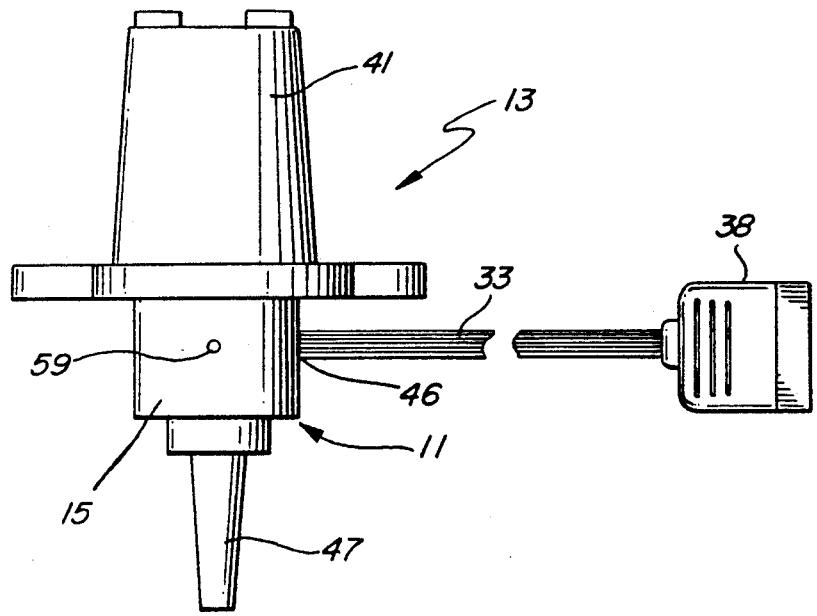
FIG. 5 is a top view of the endotracheal tube connector of FIG. 1.

FIGS. 4 and 5 show external views of the endotracheal connector 13. The connector 13 is placed between the ventilator circuit Y or T piece and the endotracheal tube, as known in the art. The ventilator circuit side of the connector 13 consists of a male 15-mm tapered body 41. The inner diameter of the lumen 17 (FIG. 1) of the connector 13 matches the inner diameter of the endotracheal tube. In the top view of FIG. 5, the transducer interconnection cable 33 and connector 38 are visible.

Figure 6:
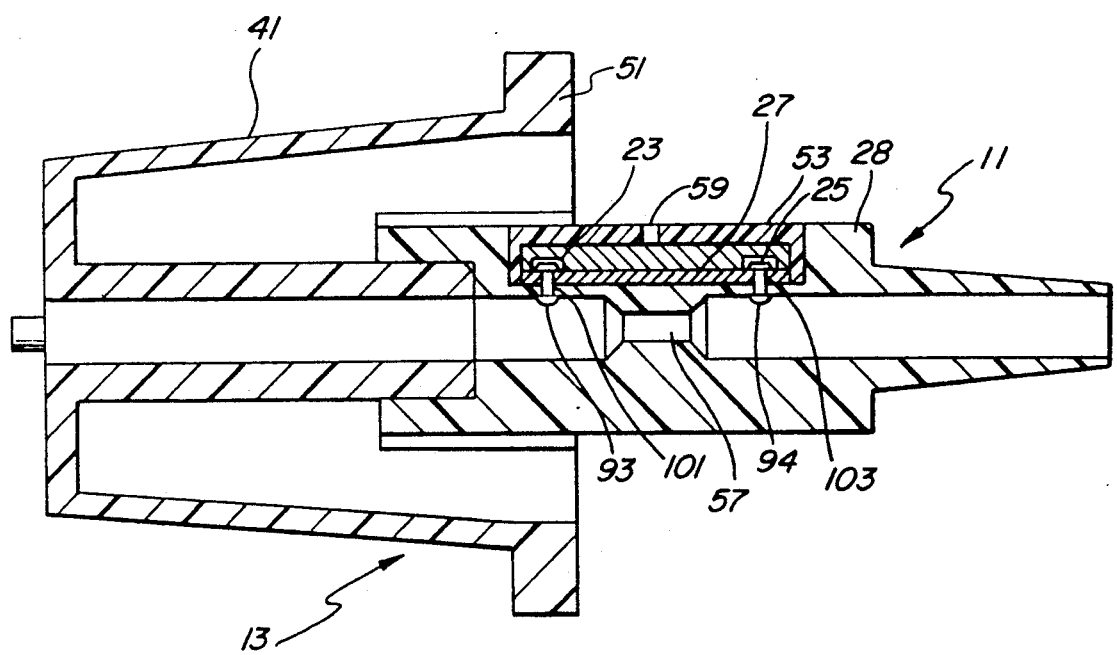
FIG. 6 is a cross-sectional schematic view taken at 6—6 of FIG. 5.

FIG. 6 is a cross-sectional view along the long axis of the ET connector 13, illustrating the ET connector body 41, the transducer subassembly 11, the transducer substrate 27, and the cap 53. The flow restriction 57 is part of the transducer subassembly 11 and is located between two ports or holes 101, 103 in the transducer substrate 27 leading to the transducers 23, 25. The holes 101, 103 are filled with silicone barrier material 93, 94, which transmit pressure to the respective transducers 23, 25, while protecting the transducers 23, 25 from contamination from exposure to the ventilator gases and moisture. The vent hole 59 in the cap 53 references the back side of the transducers 23, 25 to atmospheric pressure. The transducer cap 53 is attached, e.g. glued, to the transducer element body 28. This part design lends itself to injection molding using a plastic such as ABS, making the internal diameters of the transducer easy to reproduce. The body 28 supports the transducer substrate 27 and preferably provides a strain relief 46 for the interconnection cable 33, see FIG. 5.

CONNECTOR-ENDOTRACHEAL TUBE PNEUMOTACH

Figure 7:
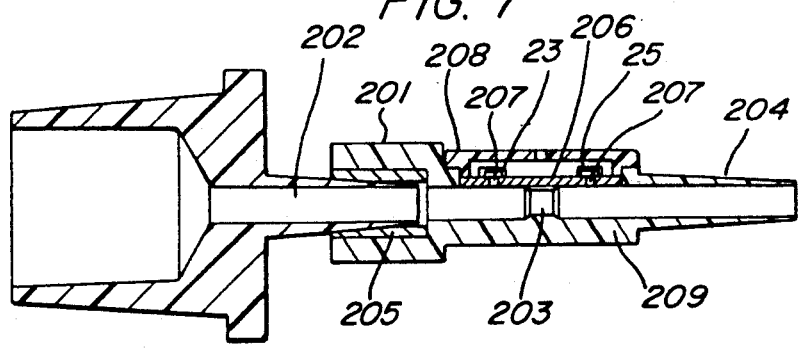
FIG. 7 is a side sectional view of a pneumotach suitable for connection between an endotracheal tube connector and an endotracheal tube.

FIG. 7 is a cross-sectional view of an alternate pneumotach according to the preferred embodiment suitable for connection between the endotracheal tube connector and the endotracheal tube. The device consists of a housing 201 that extends the lumen of an endotracheal tube connector 202. The flow restrictor 203 is a reduction in the internal diameter of the lumen of the pneumotach housing 209. The endotracheal tube is connected to the extended portion of the pneumotach 204. The pneumotach 204 is attached to the endotracheal tube connector 202 by a compliant section of tubing 205 between the housing 209 and the extension of the endotracheal tube connector 202. The pressure transducer subassembly 206 is mounted into a cavity in the housing 209. Ports 207 are molded into the housing 209 on both sides of the flow restrictor for communication to the pressure transducer(s). A cap 208 covers the pressure transducer subassembly. The pressure transducer(s) in all the configurations are connected to appropriate measurement instrumentation through a multiconductor cable exiting out the side of the housing (not shown in figure).

The connector/tube pneumotach is sized specifically for the endotracheal tube and connector with which it is intended to be used. Consequently, the size of restriction employed can be chosen to optimize the linearity and sensitivity of the transducer for the range of clinically encountered flows of the patient who would use that size endotracheal tube.

IN-LINE ADAPTER PNEUMOTACH

Figure 8:
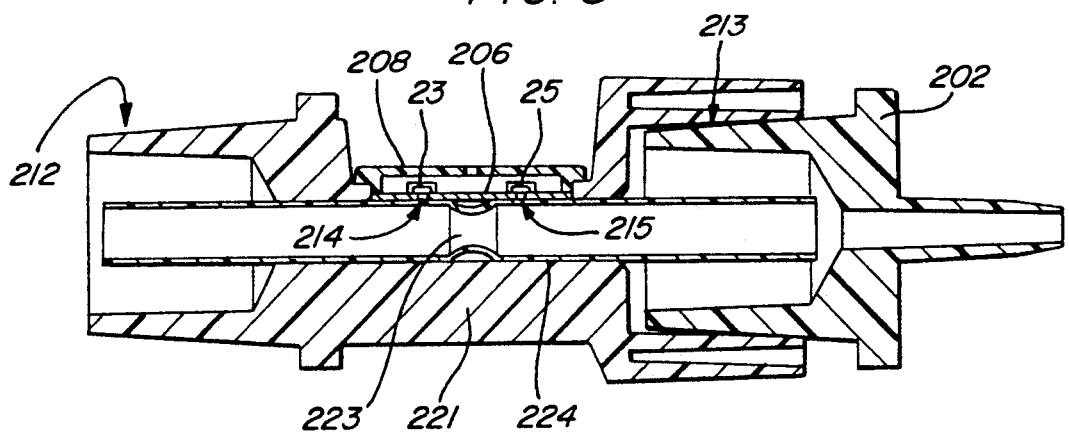
FIGS. 8 and 9 are side sectional views of in-line pneumotach embodiments.
Figure 9:
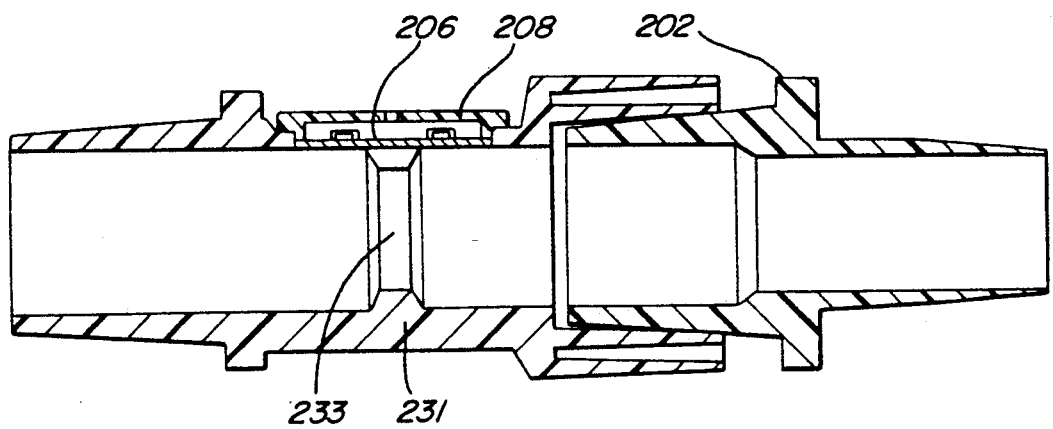

FIGS. 8 and 9 are cross-sectional views of an in-line pneumotach. This device is designed to fit between the "Y" piece and the endotracheal tube connector 202. The in-line adapter consists of a housing 221 with a male ventilator circuit taper 212 on the end fitting into the "Y" piece and a female ventilator circuit taper 213 into which fits the endotracheal tube connector 202. In both drawings, the transducer subassembly 206 is mounted in a cavity in the housing 221 and the transducer cap 208 covers the transducer subassembly.

The in-line pneumotach is designed with a range of flow path diameters to cover the sizes of the endotracheal tubes and connectors. Maintenance of a consistent flow path diameter from the endotracheal tube, through the endotracheal tube connector, and through the body of the in-line pneumotach is accomplished by insert molding a thin-walled tube 224 in FIG. 12 in the lumen housing 221. A reduced internal diameter flow restrictor 223 is roll formed into the tube by a conventional roll forming process, and holes 214, 215 are punched through the wall on both sides of the reduced diameter section for communication of pressure to the pressure transducers 23, 25. One end of the tube 224 extends into the female tapered side 213 of the pneumotach housing 221 and approaches, but does not touch, the back side of the endotracheal tube connector 202. The extended tube 224 confines gas flow from the endotracheal tube, through the endotracheal tube connector 202, and into the lumen of the thin-walled tube 224. The opposite end of the tube 224 extends into the male side 212 of the pneumotach housing 221 to reduce the dead space in the male part 212 of the device and to improve the linearity of the pneumotach.

Figure 13:
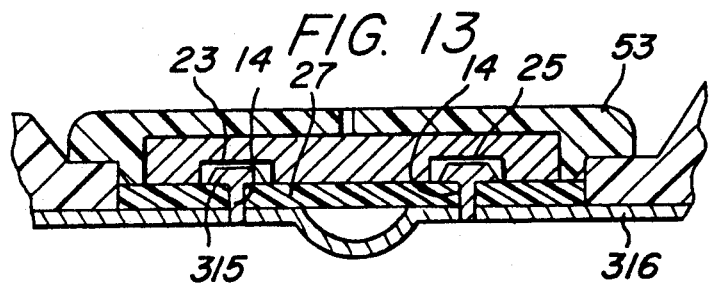
FIGS. 13-16 illustrate side sectional views of respective pressure transducer arrangements.

One embodiment of a large size in-line pneumotach is shown in FIG. 13. This embodiment does not employ the tube 224, and the restrictor with a reduced internal lumen diameter 223 may be molded in as part of the housing 231.

Different sizes of thin-walled tubes can be placed in the in-line connector to match the internal diameter of the endotracheal tube. Presenting a consistent internal diameter flow path through the in-line connector/pneumotach reduces turbulent flow through the device and optimizes measurement linearity for the respiratory flow range clinically encountered up to the largest size where the tube may not be needed.

ELBOW PNEUMOTACH

Figure 14:
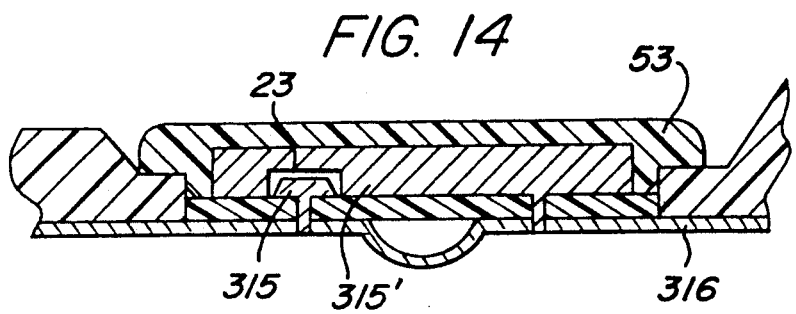
Figure 15:
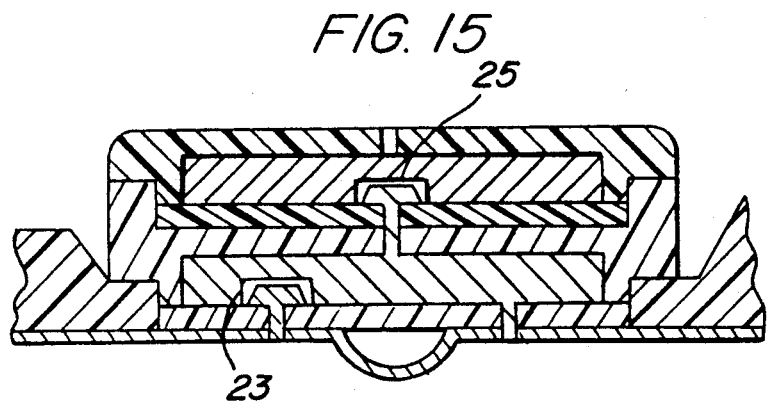

Two configurations of elbow pneumotachs are shown in FIGS. 10 and 11. The difference between the configurations is the location of the pressure transducer subassembly 206 and the restrictor 243. The housings 241, 251 are in the form of a ventilator circuit elbow employing respective male and female ventilator circuit tapers 246, 248. The male taper 246 fits into the "Y" piece, while the endotracheal tube connector fits into the female elbow taper 248. In FIG. 14, the flow restriction and transducer subassembly are placed closest to the female tapered connection 248. In FIG. 15, the flow restriction and transducer subassembly are placed closest to the male tapered connector 246. In each embodiment, gas flow through the elbow connector is confined to the lumen of a respective thin-walled tube 245, 255 molded into the device. The respective flow restrictors 243, 253 are roll formed into the wall of the respective tubes 245, 255, and holes 240, 250 are punched through the tube walls for communication of pressure on both sides of the respective restrictors 243, 245 to the pressure transducers 23, 25. As in the in-line pneumotach, the elbow pneumotach incorporates different sizes of thin-walled tubes to present a consistent flow path diameter.

"Y" PIECE PNEUMOTACH

Figure 12:
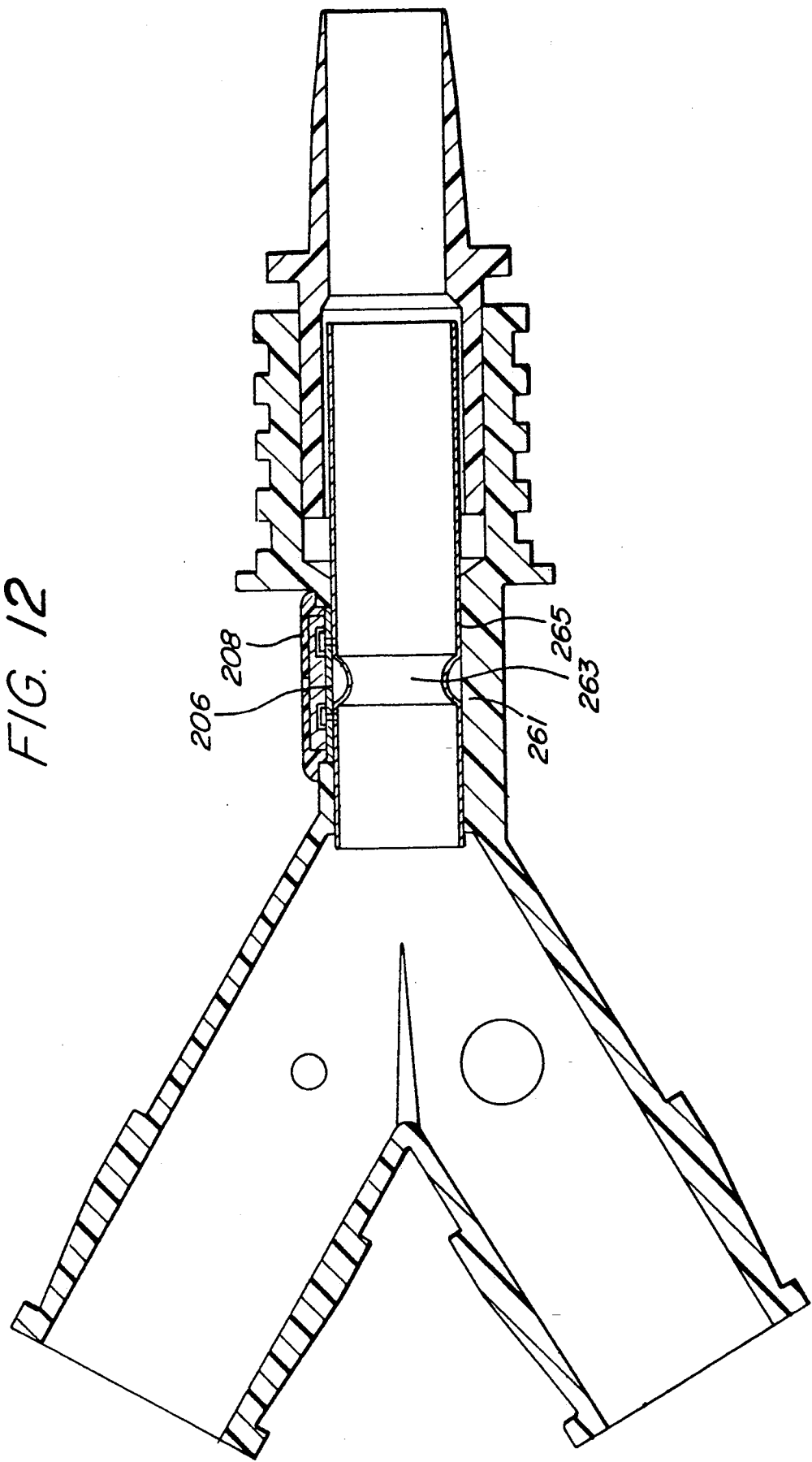
FIG. 12 is a side sectional view of a Y-piece pneumotach according to the preferred embodiment.

An embodiment of a pneumotach placed in the common leg of the "Y" or "T" piece as shown in FIG. 12 The housing 261, in the form of the "Y" piece, has an extended common leg onto which is added a cavity for the transducer subassembly 206. A thin-walled tube 265 is again employed to conduct the gas flow and present a flow restriction 263. Again, the tube 265 may be sized to match the internal diameter of the endotracheal tube and to optimize the measurement linearity.

PRESSURE TRANSDUCER CONFIGURATIONS

FIGS. 13 through 16 show a transducer subassembly with two pressure transducers. The pressure transducers 23, 25 are mounted on a substrate material 27, preferably alumina, see FIG. 3. Holes 101, 103 are drilled through the substrate 27 under the transducers 23, 25 for communication of pressure to the etched diaphragm of the transducer 23, 25. A gel substance 315 fills the space under the transducers, the holes 101, 103 through the substrate and the tube 316 for transmission of pressure and to prevent exposure of the transducers 23, 25 to the respiratory gases and water. The transducer chips are wire bonded to the substrate 27. Trimming resistors are deposited on the substrate to match the transducers for offset, span, and temperature sensitivity. A flexible cable (FIG. 5) is attached to the substrate for connection to the monitoring instrumentation.

Two transducers 23, 25 in FIG. 13 measuring gauge pressure before and after the flow restrictor allow measurement of gauge proximal airway pressure off of any one transducer. The pressure difference is calculated by analog or digital subtraction of the two measured gauge pressures in the measurement instrument. The proximal airway pressure measurement is used to calculate airway resistance and ventilatory compliance when used in conjunction with the ventilatory flow and derived ventilatory volume data originating from the differential pressure determination. Since gauge pressure is being measured, the transducer cap 53 is vented to atmosphere.

A single transducer 23 can be employed as shown in FIG. 14. In this configuration, the difference in pressure across the flow restrictor is mechanically sensed by application of the pressures on opposite sides of the transducer diaphragm. The transducer cap 53 is not vented. Pressure is transmitted from one port by the gel media 315 to the top side of the transducer and from the other port by different gel media 315' through the substrate to the bottom side of the transducer. In this configuration, the gauge proximal airway pressure measurement cannot be made. This configuration is sufficient if just ventilatory flow and volume data is needed from the pneumotach.

Figure 16:
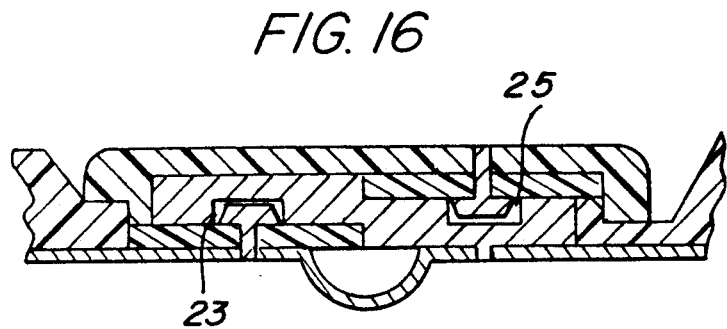

FIGS. 15 and 16 show transducer configurations where the transducers 23, 25 are mounted on two separate substrates. One transducer 23 senses the pressure difference, while the other transducer 25 senses the gauge pressure.

In all cases, the pressure transducers 23, 25 are part of the pneumotach housing, eliminating the pressure tubes employed in the prior art to conduct the pressure wave from the flow restrictor to the transducer. This design does not allow water to accumulate in any of the pressure conducting pathways, thereby maintaining accuracy of flow measurements in the presence of condensed water.

In summary, the pneumotach designs presented in this disclosure represent an improvement over the prior art by incorporating the pressure transducer(s) onto the housing of the flow measurement device. The flow transducer configurations cover all elements of the ventilator circuit with a common inspiratory and expiratory path. The benefit of this design is elimination of problems associated with pressure conducting lines to a remote pressure transducer. Low cost pressure transducer subassemblies allow the pneumotach to be discarded after a single patient use, eliminating cross-contamination problems and the costs of cleaning the device A single pressure transducer design is sufficient for ventilatory flow and volume measurements. Pressure transducer subassemblies configured with two gauge sensing transducer subassemblies configured with two gauge sensing transducers or one differential and one gauge sensing transducer allows measurement of many pulmonary mechanics measurements. Combining ventilatory volume data with gas analysis data from other instruments generates useful metabolic and anesthetic data. Combining metabolic data with blood gas and pressure data yields useful cardiovascular data.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An apparatus for use in combination with an endotracheal tube for insertion into a patient and a ventilator device for providing a ventilatory gas flow to the patient, the apparatus located between the endotracheal tube and the ventilator device, the apparatus comprising:

a ventilator circuit element having a passageway for gas flow between the endotracheal tube and the ventilator tube;

flow restrictor means in said passageway for developing a differential pressure;

first and second openings in said element on either side of said flow restrictor means communicating with said passageway;

pressure transducer means integral to the circuit element and located opposite at least one of said first and second openings; and means filling said openings for communicating said differential pressure to said pressure transducer means.

2. The apparatus of claim 1 wherein said filling means comprises a gel-like substance filling said openings and contacting said transducer means.

3. The apparatus of claim 1 wherein said transducer means comprises a pair of strain gauges.

4. The apparatus of claim 3 wherein said gauges each have a curved side and a flat side, each said curved side being disposed opposite said openings.

5. The apparatus of claim 3 wherein each gauge in said pair is mounted on a different substrate.

6. The apparatus of claim 1 wherein said pressure transducer means comprises a single semiconductor strain gauge in a differential mode.

7. The apparatus of claim 1 wherein said ventilator circuit element comprises an in-line element having means at a first end for connecting to a ventilator circuit "Y" piece and means at an opposite end for connecting to an endotracheal tube connector.

8. The apparatus of claim 1 wherein said ventilator circuit element includes means for connecting it between an endotracheal tube connector and said endotracheal tube.

9. The apparatus of claim 1 wherein said ventilator circuit element comprises an elbow pneumotach.

10. The apparatus of claim 1 wherein said ventilator circuit element comprises a "Y"-piece pneumotach.

11. An endotracheal tube connector for use in combination with an endotracheal tube for insertion into a patient and a ventilator device for providing a ventilatory gas flow to the patient, the endotracheal tube connector located between the endotracheal tube and the ventilator device, the endotracheal tube connector comprising:

a connector body having a lumen for gas flow between the endotracheal tube and the ventilator device;

flow restrictor means in said lumen for developing a differential pressure;

first and second openings in said body on either side of said flow restrictor means communicating with said lumen; and semiconductor pressure transducer means integral to the connector body and operationally connected to said openings for developing an electrical signal representative of said differential pressure.

12. An endotracheal tube connector for use in combination with an endotracheal tube for insertion into a patient and a ventilator device for providing a ventilatory gas flow to the patient, the endotracheal tube connector located between the endotracheal tube and the ventilator device, the endotracheal tube connector comprising:

a connector body having a lumen for gas flow between the endotracheal tube and the ventilator device;

flow restrictor means in said lumen for developing a differential pressure;

first and second openings in said body on either side of said flow restrictor means communicating with said lumen;

pressure transducer means integral to the connector body and operationally connected to said openings; and means filling said openings for communicating said differential pressure to said pressure transducer means.

13. The endotracheal tube connector of claim 12 wherein said filling means comprises a gel-like substance filling said openings and contacting said transducer means.

14. The endotracheal tube connector of claim 13 wherein said pressure transducer means comprises a pair of strain gauges.

15. The endotracheal tube connector of claim 14 wherein said gauges each have a curved side and a flat side, each said curved side being disposed opposite said openings and in contact with said gel.

16. The endotracheal tube connector of claim 15 wherein said pressure transducer means comprises a single semiconductor strain gauge in a differential mode.

* * * * *